United States Patent
Williams

(10) Patent No.: US 9,414,790 B2
(45) Date of Patent: Aug. 16, 2016

(54) DUAL-ENERGY CONE-BEAM CT SCANNING

(71) Applicant: Elekta AB (publ), Stockholm (SE)

(72) Inventor: Malcolm Williams, Stockholm (SE)

(73) Assignee: Elekta AB (Publ), Stockholm (SE)

( * ) Notice: Subject to any disclaimer, the term of this patent is extended or adjusted under 35 U.S.C. 154(b) by 282 days.

(21) Appl. No.: 13/651,818

(22) Filed: Oct. 15, 2012

(65) Prior Publication Data

US 2014/0105352 A1    Apr. 17, 2014

(51) Int. Cl.
| | |
|---|---|
| *A61B 6/03* | (2006.01) |
| *A61B 6/04* | (2006.01) |
| *A61B 6/00* | (2006.01) |
| *A61N 5/10* | (2006.01) |

(52) U.S. Cl.
CPC .............. *A61B 6/0421* (2013.01); *A61B 6/405* (2013.01); *A61B 6/482* (2013.01); *A61N 5/1049* (2013.01); *A61N 2005/1061* (2013.01)

(58) Field of Classification Search
USPC ............................................................ 378/5
See application file for complete search history.

(56) References Cited

U.S. PATENT DOCUMENTS

| | | | | |
|---|---|---|---|---|
| 5,175,754 | A * | 12/1992 | Casey ................... | A61B 6/035 378/101 |
| 7,209,537 | B2 * | 4/2007 | Popescu ................. | A61B 6/032 378/108 |
| 7,606,345 | B2 * | 10/2009 | Nishide .................. | A61B 6/032 378/13 |
| 2010/0183117 | A1 * | 7/2010 | Tsumuraya et al. ............... | 378/9 |
| 2011/0200164 | A1 * | 8/2011 | Blaj .................................. | 378/4 |
| 2012/0114094 | A1 * | 5/2012 | Shapiro .................. | A61B 6/032 378/19 |

* cited by examiner

*Primary Examiner* — Phillip A Johnston
*Assistant Examiner* — Hsien Tsai
(74) *Attorney, Agent, or Firm* — Sunstein Kann Murphy & Timbers LLP

(57) ABSTRACT

A CT scanning apparatus includes a control apparatus arranged to cause a first rotation of a gantry and trigger an x-ray source to emit x-radiation at a first x-ray energy when an angular encoder reports that the gantry is at each of multiple predetermined angular locations, and cause a second rotation of the gantry and trigger the x-ray source to emit x-radiation at a second x-ray energy differing from the first x-ray energy when the angular encoder reports that the gantry is at each of the same predetermined angular locations. An image processing means receives the projection images and reconstructs them into a volumetric image. A support couch is provided for the patient, and to minimize the likelihood of movement artifacts, the support couch includes a patient immobilisation system such as an evacuatable bead bag, bite post, or stereotactic frames, or the like.

13 Claims, 4 Drawing Sheets

DUAL-ENERGY CONE-BEAM CT SCANNING

FIELD OF THE INVENTION

The present invention relates to dual-energy cone-beam CT (computed tomography) scanning.

BACKGROUND ART

Computed tomography techniques were first suggested in the 1960s, with practical implementation beginning in the 1970s. The essential principle is that a number of projections are obtained from a number of rotational directions around a single axis of rotation, showing the x-ray attenuation after passing through the object under investigation. Computational techniques are applied to this plurality of projections, to yield a three-dimensional image of the interior of the object. Contrast in the image is derived from the different attenuation rates of the different materials making up the object, and the overall image quality is dependent on the provision of an adequate number of projections. The basic process is set out in U.S. Pat. No. 3,106,640 but has been developed considerably since then.

Typically, a CT scanner will comprise an x-ray source mounted in a rotateable manner around an axis, such as on a ring or a gantry, together with either a single detector mounted opposite the source or a plurality of detectors arranged around the ring. The scanner will be rotated around the axis and will emit pulses of radiation at a predetermined frequency, i.e. with a predetermined time period between them. These pulses will then be detected after attenuation and the resulting series of projections used to compute an image.

The source may be a fan beam directed toward a linear array of detectors, or a cone beam directed towards a two-dimensional detector array. Often, a dedicated investigative CT scanner will use a fan beam illuminating a linear array in order to yield a high-quality image. Such scanners often rotate at a high speed around the patient (or object) under investigation in order to produce an image within a short period of time and to minimise movement artefacts in the image.

Other CT arrangements include a cone-beam arrangement mounted on or as part of the gantry of a radiotherapy apparatus, with the aim of combining radiotherapeutic treatment with obtaining a CT scan. The results of the CT scan can then confirm accurate positioning of the patient and/or guide the radiotherapy delivery. In such cases, the rotational speed of the CT scanner is often dictated by the rotational speed of the radiotherapy gantry, and may be as low as 1 rpm. Such combined systems may use a separate kV x-ray source of CT mounted (for example) 90° away from the therapeutic source, or may rely on a single source able to switch between diagnostic kV emissions and therapeutic MV emissions. Sometimes, a limited form of CT ("portal CT") is possible using images derived from the therapeutic beam after attenuation by the patient, but the overall contrast of such images is poor given that there is less difference in attenuation coefficients between different materials at the very high energies involved in the therapeutic beam.

Our earlier patent application WO2012/103901 described such a CT system which dealt with the problem that activation of the diagnostic source at a steady frequency might result in unnecessary dosage being delivered to the patient, given that rotation of the gantry was dependent on the needs of the therapeutic source. At times, the rotation rate might be very low or zero, resulting in the production of projection images that were by and large redundant. Our application therefore explained that the diagnostic source should be gated to wait for a minimum angle of rotation to take place between successive images. Gantries are provided with built-in electronics to detect the gantry angle, so the information is readily available.

CT scanning offers good resolution between markedly different material types, such as between bone and soft tissue. However, the attenuation of x-rays by different types of soft-tissue is very similar and therefore CT scans tend to offer poor contrast within soft-tissue areas. One way of addressing this is to employ dual-energy scanning, in which a first set of projection images are obtained at a first x-ray energy such as 80 kVp and a second set are obtained at a second and different x-ray energy such as 140 kVp. These two energies are chosen as they are often the upper and lower limits of the energies available for selection. The x-ray attenuation of materials varies with the x-ray energy, as noted above in relation to portal CT, and this difference in energy is enough to allow different materials to be distinguished by their different differential attenuation. The resulting volumetric image can therefore be marked to identify areas of different materials, such as by artificial colours or by tagging them so that specific material types can be highlighted or removed from the image. A summary of the development of dual-energy CT scanning techniques can be found in the article "An Introduction to Dual Energy Computed Tomography" by Michael Riedel, University of Texas Health Science Center at San Antonio published online at http://ric.uthscsa.edu/personalpages/lancaster/DI2_Projects_2010/dual-energy_CT.pdf.

Dual energy CT scanners therefore typically comprise two kV tubes, operating at two different energies, and mounted on the same rotating mount by separated by a suitable angular separation. Rotating at high speed around the patient, a set of projection images are obtained at both energies. Older dual energy systems employed a single source that made multiple passes around the patient at different energies, but suffered from difficulties arising from natural movement of the patient between passes. The successful implementation of dual energy CT scanning therefore had to wait for the ability to integrate multiple sources into a single apparatus.

SUMMARY OF THE INVENTION

We wish to integrate dual energy CT techniques into a cone-beam CT unit operating as part of a radiotherapy apparatus. Such CT devices tend to use either a second kV tube (for example, located on the gantry 90° from the main radiotherapy head) or via a source that can vary its output energy from a chosen kV output level suitable for diagnosis to an MV level suitable for treatment. Both types of source are suitable for the present invention.

The present invention therefore provides a CT scanning apparatus comprising a gantry, rotateable about an axis of rotation, an x-ray source mounted on the gantry at a location offset from the axis of rotation, and capable of emitting x-radiation at a selected one of at least two different x-ray energies, a detector for the x-ray source, mounted opposite the source thereby to detect the x-rays after attenuation by an investigative subject located substantially at the axis of rotation, an angular encoder for detecting an angular position of the gantry, and a control apparatus with control over rotation of the gantry and over operation of the x-ray source, able to receive information from the angular encoder, wherein the control apparatus is arranged to cause a first rotation of the gantry and trigger the x-ray source to emit x-radiation at a first x-ray energy when the angular encoder reports that the gantry is at each of a plurality of predetermined angular locations, and cause a second rotation of the gantry and trigger the x-ray source to emit x-radiation at a second x-ray energy differing from the first x-ray energy when the angular encoder reports that the gantry is at each of the same plurality of predetermined angular locations.

Generally speaking, the gantries of therapeutic apparatus rotate significantly more slowly than do the sources of a purely investigative CT scanner. As a result, such angle-based triggering is viable, and allows the projection images at each of the two energies to be taken from the same angle. This avoids the complex mathematics needed by existing solutions which capture projections at a specified frequency and at alternating high and low energies; that processing leads to noise and (ultimately) poorer quality pictures which is avoided by the present invention.

It does not make a significant difference which direction the gantry is moving when the projection image is captured. Thus, we prefer that the first rotation and the second rotation are in opposite directions. Ideally, the second rotation returns the gantry to the state from which the first rotation commenced. This allows the second set of projections (at the second energy) to be captured on the return sweep of the gantry, meaning that no additional time is required in order to provide a dual energy capability.

An image processing means can be provided in order to receive the projection images and reconstruct them into a volumetric image. This can be arranged to combine the output of the detector from the first and the second rotations to create at least one further projection image for each of the predetermined angles, and then reconstruct a volume image from the set of further projection images. Alternatively, it can be arranged to reconstruct a first volume image from the projection images produced by the detector during the first rotation and reconstruct a second volume image from the projection images produced by the detector during the second rotation and produce a combined volume image from the first volume image and the second volume image.

A support couch is usually provided for the patient, to locate the patient substantially at the axis of rotation. To minimise the likelihood of movement artefacts, we prefer that the support couch comprises a patient immobilisation system. Examples of such systems include evacuatable bead bags, bite posts, and stereotactic frames. It is relatively common to provide such systems in a therapeutic context in order to deliver the therapeutic beam accurately, and therefore these can be taken advantage of to provide for an accurate dual-energy CT scan.

The predetermined angles can be spaced in a substantially regular manner.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
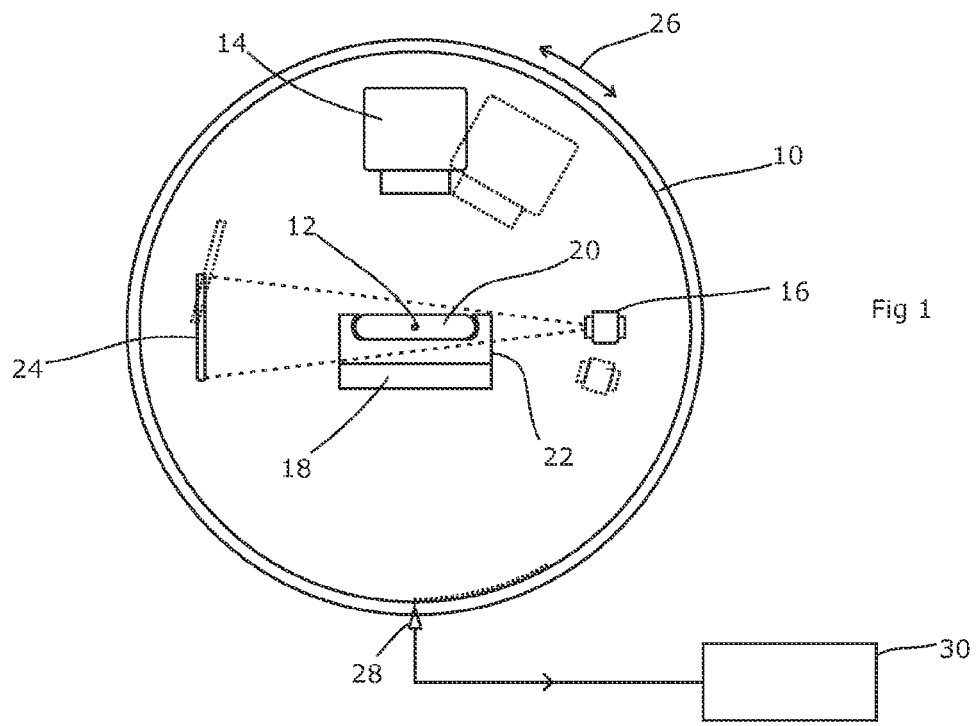
FIG. 1 shows a view from the front of a suitable form of radiotherapy apparatus.

The present invention has as its aim a way of implementing dual energy methods to reduce artefact and distortion in CBCT images taken using slow-moving gantries such as those used for the delivery of radiotherapy.

Dual energy CT is a known technique for fast-moving gantries such as are available for dedicated CT imaging systems, where the gantry movement serves the CT system only and can thus be tailored around it. In certain designs of therapeutic radiotherapy devices, however, the gantry must carry (or also carry) a therapeutic source able to deliver high-energy x-rays (1 MV or greater), which has a significant weight and which must be positioned to a high degree of accuracy. A high-speed gantry is therefore not practical in such cases, and is in any case not necessary for the therapeutic source. Such gantries therefore tend to move at low rotational speeds such as 1 rpm or so.

In known dual-energy CT systems, the source is triggered to produce a projection image by a clock. According to the present invention, it should instead be triggered by the angle of the gantry. There are already electronics to determine the instantaneous gantry angle built in to the apparatus. This change creates several advantages in the context of a slow-moving gantry, as explained herein. In particular, in a time-triggered system the x-ray energy is quickly switched between low and high during a single sweep of the gantry. This means that the high energy pulse and the subsequent low energy pulse are not taken from exactly the same angle, as the gantry travels a short distance between these pulses. Hence the angle changes, and that leads to complicated mathematics to compensate for in the reconstruction algorithm. According to the present invention, the gantry can make a sweep with a first energy level and pulse at certain angles. Then, on the way back, the gantry can pulse with the second energy level at exactly the same angles, thereby minimizing distortion.

The angles would normally be decided upon beforehand (together with a tolerance). The CBCT system is the set in motion, and as the arm is swept past the predetermined angles the exposure is triggered. Since the direction of travel is not critical, it is most convenient to use the forward sweep for one energy level and the return sweep for the other. It does not especially matter which sweep is used for which energy level. Since the exposures are taken at the same angle the mathematics is much less and thus the picture quality is correspondingly better, and since the energies are only switched once (and not repeatedly between exposures) it can be achieved with a simpler and cheaper KV generator. Since the exposures can be taken repeatedly at the same angle, a poor quality projection image in the sequence could be retaken without having to perform the entire sequence again. Also, as the system is angle-driven, it no longer is dependent on a smooth and constant speed of the motor and is not affected by slack in the drive train.

Figure 2:
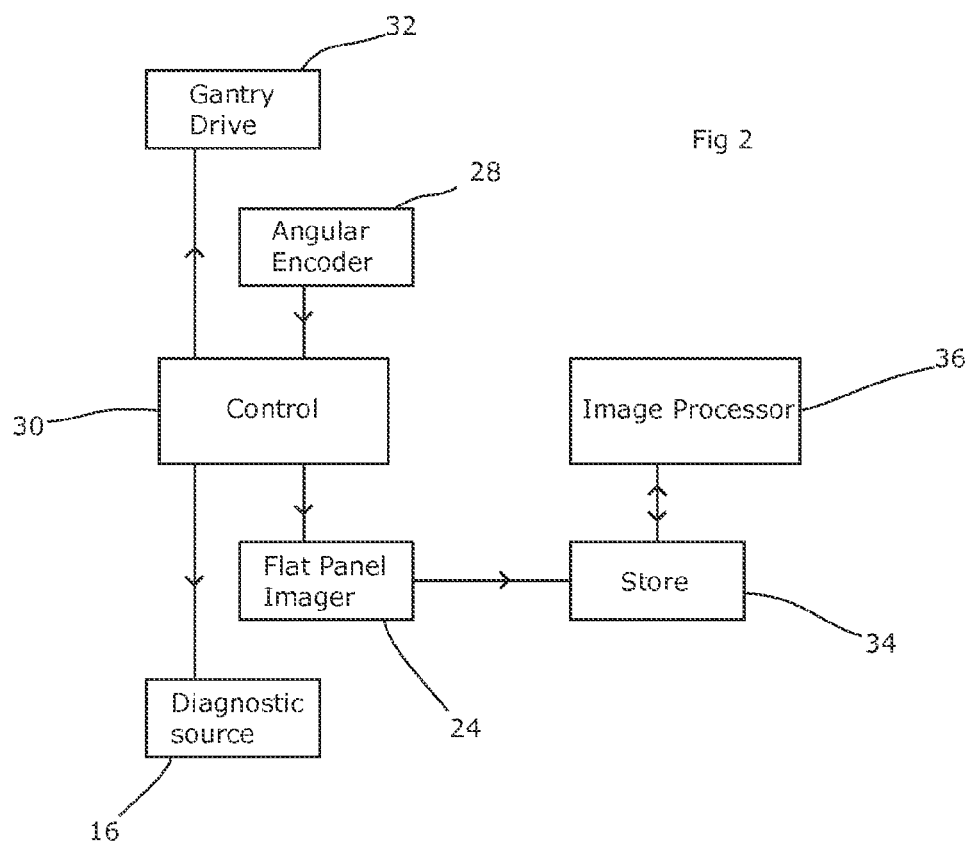
FIG. 2 shows the functional links called for by the present invention.
Figure 3:
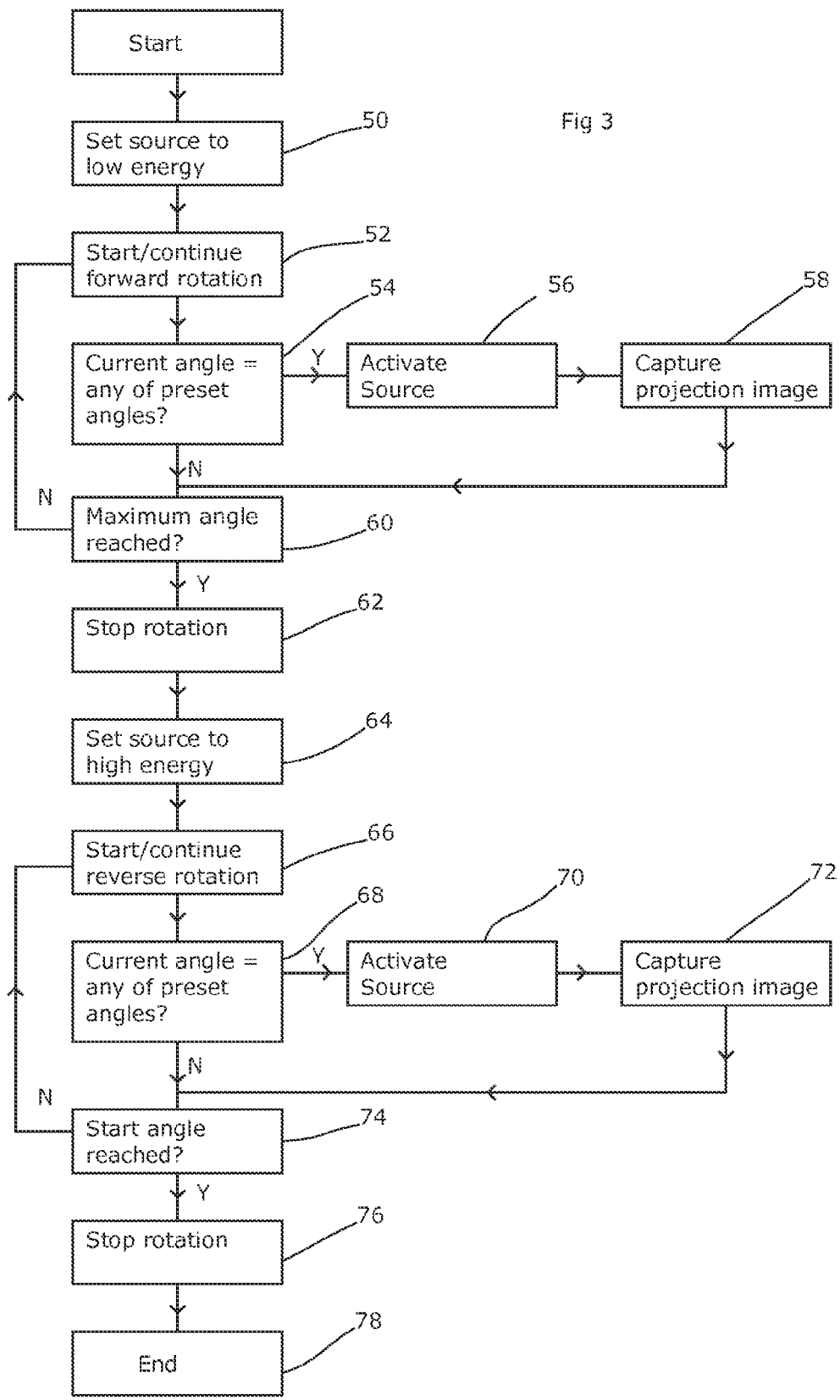
FIG. 3 shows a flowchart of the process adopted by the present invention.

An example of a possible implementation of this idea is shown in FIGS. 1 to 3. This is a dual energy CBCT system integrated into a radiotherapy delivery apparatus, in which a rotateable gantry 10 is mounted to a suitably secure foundation and rotataeable around a central horizontal axis 12, driven by a drive motor (not shown). It carries a therapeutic x-ray source 14 and a diagnostic x-ray source 16 spaced from the therapeutic source 14 by a 90° rotation around the axis 12. Both sources emit a radiation beam towards the axis 12, just below which there is a patient couch 18 on which a patient 20 can be placed and kept in position by an immobilisation system such as an evacuated bead bag 22 (shown schematically and described in more detail below).

A flat-panel imager 24 is also provided on the gantry, opposite the diagnostic source 16 in order to detect x-radiation emitted from that source after attenuation by the patient 20. The entire assembly of the gantry 10, therapeutic source 14, diagnostic source 16 and flat-panel imager 24 rotates together around the axis 12 as shown by arrow 26 and the dotted-line representations. An angular encoder 28 measures the instantaneous angle of the gantry 10 and reports this angle to a control unit 30 which is able to send movement commands to the drive motor and trigger commands to at least the diagnostic source 16 and the flat panel imager 24.

The control unit 30 is based around a Field-programmable Gate Array ("FPGA") which is programmed to read the angle of the CBCT arm repeatedly from the angular encoder 28 at around 1000 Hz. The FPGA is pre-loaded with an array of angles, which it uses together with the actual angle information to send out a trigger pulse to the diagnostic kV source 16, and the same or a separate delayed pulse to the flat panel imager 24 to tell it to read the new exposure.

The logical connections to and from the control unit 30 are shown in FIG. 2. The control unit 30 receives information from the angular encoder 28, as noted above. As and when dictated by the programming of the FPGA (in the control unit 30), trigger signals can be sent to the diagnostic source 16 and the flat panel imager 24. Drive commands can also be sent to the gantry drive 32. The flat panel imager sends the projection image that it obtains to a data store 34 together with the angle information derived from the angular encoder 28 (provided to it via the control unit 30). Once in the data store, the projection images can be accessed by an image processor 36 that reconstructs volumetric images from the individual projection images.

FIG. 3 shows a flowchart for the control process according to the invention. The diagnostic source 16 is initially set to its "low" energy setting, box 50. This assumes that the low energy projections will be captured first, and the higher-energy projections captured second. This could of course be reversed if preferred. The gantry 10 is then instructed to start rotation (box 52) and the control unit 30 starts to monitor the output of the angular encoder 28 to see if the gantry is currently at any of the preset angles (box 54). If so, the diagnostic source is triggered to produce a pulse of radiation (box 56) and the flat panel imager is read to obtain the projection image (box 58) which is then passed to the file store 34 for later reconstruction. The control unit then checks to see if the planned maximum angle of rotation (usually 180° or 360°) has been reached (box 60) and, if not, allows the rotation to continue (box 52) and carries on checking the current angle (boxes 54 and 60).

Once the maximum angle is reached, the control unit 30 instructs the gantry 10 to stop rotating (box 62). The diagnostic source 16 is then set to its higher energy setting (box 64), which may involve automatically changing one or more filters for the beam in order to take account of or put in place a different energy profile for the beam. The control unit 30 then instructs the gantry 10 to begin rotating in the reverse direction. The checking process to look for trigger angles and the stop angle, and triggering the source 16 and the flat panel detector 24, then continue in the same manner as for the low energy phase (boxes 68, 70, 72, 74). Once the control unit 30 detects that the gantry 10 has returned to its original angle and thus completed both sets of projections (box 74), the rotation is stopped (box 76) and the process ends (box 78).

One of the reasons that CBCT projections have hitherto been acquired on a 'time' basis is because it is important to synchronise the kV (diagnostic) triggering with the timing of the imager readout. Typically, the kV pulse is triggered to occur between frame readouts, otherwise artefacts begin to appear in the images. Thus, the image detector readout timing is used as the 'master clock' for the trigger synchronisation. In the method of the present invention, there are a number of ways around this. An alternative master clock could be provided, and the image detector readout triggered in response to the source being triggered (as set out in FIG. 3). Alternatively, if the image detector is still reading out a previous frame when the diagnostic source is triggered then the angle in question could be skipped in favour of the next designated angle. Some care may then be needed in choosing the predetermined angles carefully so that the various triggers synchronise correctly.

A further alternative is for the panel 24 to be pre-programmed to delay the picture gathering until a set time after the exposure, say 40 ms after the trigger, or for the control unit 30 to be programmed to set a separate trigger for the panel 24, which would occur at a programmed time after the angle trigger. Such an 'exposure delay' arranged to trigger the panel to work in what is essentially a slave mode is known, and usually involves the control unit sending a trigger to the KV generator and then waiting for the preset time before sending a red signal to the panel.

A realistic example is to have an image capture device that is capable of running at 20 Hz. A realistic exposure time for a 90 kV X-ray device is around 20 ms, and a reasonable exposure delay time for an exposure of 20 ms is about 30 ms. A realistic time to read the angle encoder is of the order of 100 us, which at a gantry rotation rate o 10°/s corresponds to an angle of 0.001°. Thus, reading the panel at 20 Hz, if the gantry arm rotates at 10 degrees per second then taking one picture per degree would be the equivalent of a 10 Hz exposure rate, or one frame every 100 ms. Since a 20 Hz panel takes around 50 ms to read the image, and the exposure delay is here 30 ms, then the spare time is about 20 ms. Processing of the projection images can be done in parallel, allowing a processing time corresponding to the time between frames, i.e. 100 ms in this example.

To improve further the correlation between the two sets of images, care can be taken in the definition of the "angle" at which the image is captured. As the gantry is rotating while the kV diagnostic beam is triggered, and the kV pulse lasts a finite time, the 'exposure angle' will actually be a range between two angles. These can be calculated beforehand since the speed and the time is known. For example, an exposure time of 30 ms at a rotation speed of 10°/s implies an angular range during the exposure of 0.3°. To compensate for this, the trigger angle in the forward direction can be defined as the start of range and the trigger angle in the reverse direction can be defined as the end range angle. This will result in two near identical projections, making the maths very much simpler.

Figure 4:
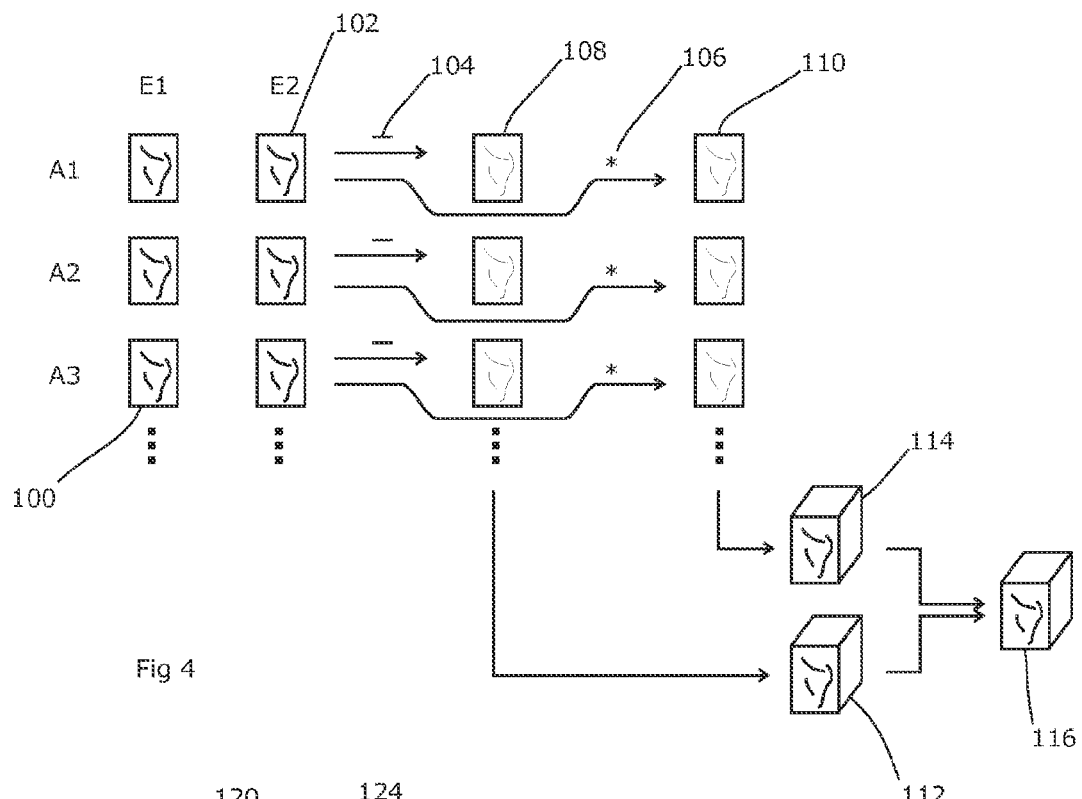
FIG. 4 shows one method for processing the images
Figure 5:
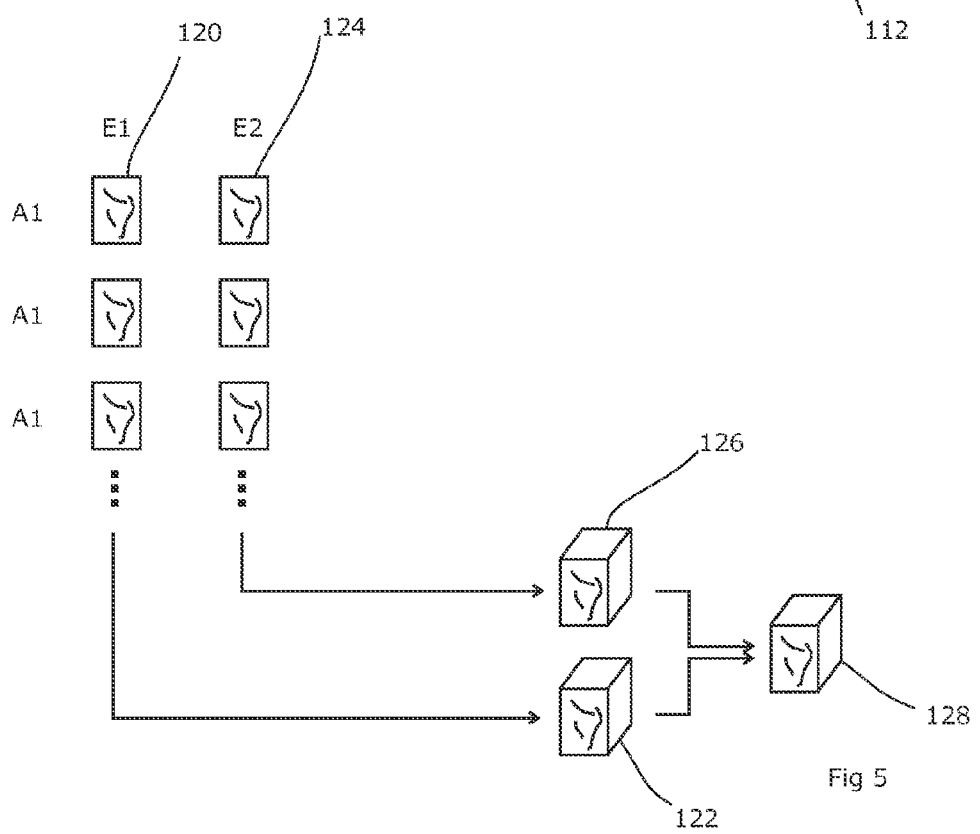
FIG. 5 shows an alternative method for processing the images.

There are (generally speaking) 2 alternative ways of doing dual energy CT processing: either pre-reconstruction or post-reconstruction, shown in FIGS. 4 and 5 respectively. Each starts with the same data from the store 34, i.e. a set of matched pairs of projection images 100, each pair consisting of an image at each of the two energy levels E1 and E2 at a single angle Ax. With pre-reconstruction approach (FIG. 4), all of the individual dual-energy projections pair are combined/decomposed into one or more new sets of projections, typically two such sets, which are then reconstructed into processed 'output' volumes. Thus, each matched pair 102 is subject to one or more combinatory functions such as subtraction 104 and/or convolution 106 that yields a number of output projection images 108, 110 corresponding to the number of functions applied. These sets 108, 110 can each be reconstructed into a corresponding volume image 112, 114. These can be viewed alternately, or can themselves be compared and combined to produce a single volume image 116, as desired.

With post-reconstruction methods (FIG. 5) all of the low-energy projections 120 are reconstructed into a low-energy volume 122, and all of the high-energy projections 124 are reconstructed into a high-energy volume 126. The combination/decomposition processing is then performed on these two volumes 122, 126 to produce the required output volume(s) 128.

The advantage of having angle-matched pairs will therefore evidently be more of significant in the context of pre-reconstruction decomposition. Post-reconstruction decomposition is much more forgiving in this regard but is likely still to benefit from matched pairs in that a difference between the volumes is then more clearly related to different attenuation characteristics rather than being an artefact resulting from the different patterns of angles in the projection images.

Figure 6:
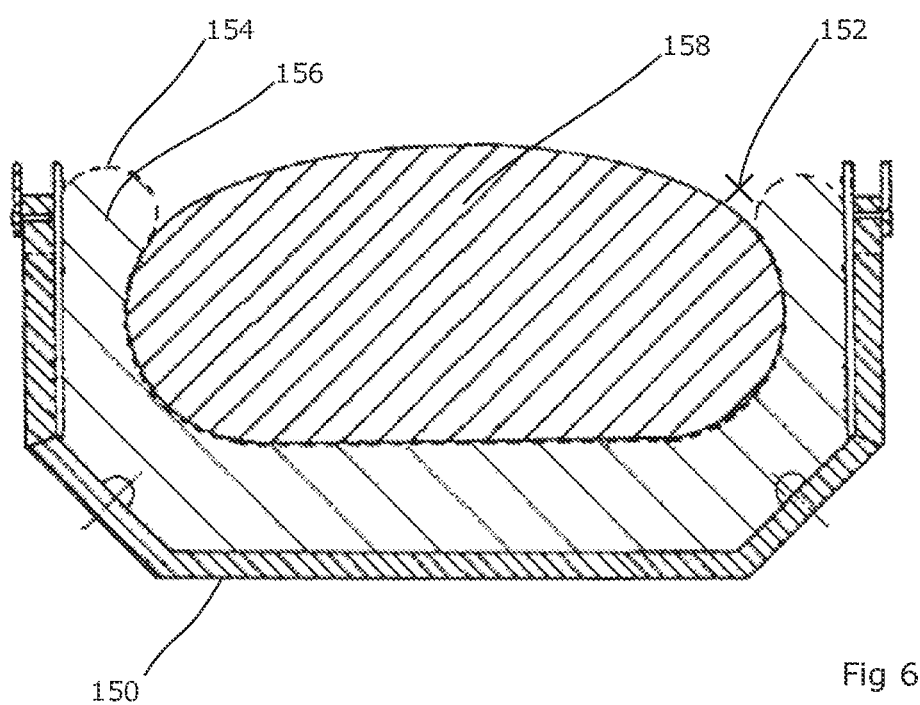
FIG. 6 shows the evacuated bead cushion immobilisation system in more detail.

We explained (above) that a patient immobilisation system is preferable in the present invention, to prevent the patient from moving between the two passes at different energies. One such system is shown in section in FIG. 6, based on an evacuateable bean bag. This includes a radiotransparent (i.e. substantially transparent to x-rays) rigid outer frame 150 which defines a trough 152 of dimensions suitable for receiving a patient. It may for example be one frame selected from a number of such frames of varying size, selected in the light of the overall dimensions of the patient to be treated. The inner part of the frame 150 is lined with a thick mattress comprising a flexible and airtight outer hull 154 loosely filled with a large number of individual beads 156. The hull 154 also has a valve (not shown) via which air can be introduced or removed from the hull interior and which can be sealed.

With the valve open and (optionally) after the introduction of air into the hull 154 so that the beads 156 are free to move within the hull 154, the patient 158 is placed on the now-soft mattress which is then manipulated to partially envelop the patient 158. An air pump is then connected to the valve and the air within the hull 154 is substantially removed, as a result of which the air pressure external to the hull 154 will compress the hull 154 onto the beads 156. This immobilises the beads 156 and renders the mattress largely rigid, fixing the patient 158 in place and preventing gross movement. The patient 158 and mattress can then be moved together via the frame 150 and placed on the couch 18 (FIG. 1).

An example of a system of this type is the Elekta Body-FIX® system.

An alternative patient immobilisation system for the head region is a bite post, such as the Elekta HeadFIX®. A suitable frame supports a post shaped to fit within the patient's hard palate. Ideally, the frame is adjustable, so that after the patient is placed in position on the couch 18, the frame can be adjusted to place the post in a comfortable location and then fixed. The patient then bites on the post, which therefore takes up a fixed position relative to the remainder of the patient's head, preventing further movement. In a refinement of this idea, internal conduits within the bite post can lead to the surface adjacent to the patient's palate, through which suction can be applied in order to urge the bite post onto the palate (or vice-versa) and allow the patient to relax. The bite post may also be individually moulded to the palate of the specific patient in question.

A further possible form of patient immobilisation is the stereotactic head frame. Some forms of cranial surgery require very precise and reliable positioning relative to the skull, for which a frame around the patient's head is fixed into place. This frame can be used to fixate the patient's head during investigative processes as well as during therapeutic steps.

Other patient fixation and immobilisation systems are available. Generally, a clinician will be able to select a suitable system in the light of the patient's needs and the specific region of the patient that is of interest.

Thus, the present invention provides a robust means for acquiring high-quality dual-energy CT scans from slow-moving gantries. It allows such imagery to be prepared from CT systems integrated into radiotherapy systems, either during radiotherapy or as a preliminary step immediately prior to radiotherapy and on the same apparatus. In that case, the CT source may be a separate x-ray source carried on the radiotherapy apparatus, or a separate mode of the same source as used for radiotherapy.

It will of course be understood that many variations may be made to the above-described embodiment without departing from the scope of the present invention.

The invention claimed is:

1. A CT scanning apparatus comprising;
a gantry, rotatable about an axis of rotation;
an x-ray source mounted on the gantry and locatable at a position offset from the axis of rotation, and capable of emitting x-radiation at a selected one of at least two different x-ray energies;
a detector for the x-ray source, positionable opposite the source thereby to detect the x-rays after attenuation by an investigative subject located substantially at the axis of rotation;
an angular encoder for detecting an angular position of the gantry;
a control apparatus with control over rotation of the gantry and over operation of the x-ray source, and able to receive information from the angular encoder;
wherein the control apparatus is arranged to:
cause a first rotation of the gantry and trigger the x-ray source to emit a pulse of x-radiation only at a first x-ray energy when the angular encoder reports that the gantry is at each of a plurality of predetermined angular locations, and
cause a second rotation of the gantry opposite in direction from the first rotation and trigger the x-ray source to emit a pulse of x-radiation only at a second x-ray energy differing from the first x-ray energy when the angular encoder reports that the gantry is at each of the same plurality of predetermined angular locations.

2. A CT scanning apparatus according to claim 1 in which the predetermined angles are spaced in a substantially regular manner.

3. A CT scanning apparatus according to claim 1 in which the second rotation returns the gantry to a state from which the first rotation commenced.

4. A CT scanning apparatus according to claim 1 further comprising an image processing means arranged to receive the output of the detector in the form of a projection image at each of the predetermined angles and reconstruct a volume image therefrom.

5. A CT scanning apparatus according to claim 4 in which the image processing means is arranged to combine the output of the detector from the first and the second rotations to create at least one further projection image for each of the predetermined angles, and then reconstruct a volume image from the set of further projection images.

6. A CT scanning apparatus according to claim 4 in which the image processing means is arranged to reconstruct a first volume image from the projection images produced by the detector during the first rotation and reconstruct a second volume image from the projection images produced by the detector during the second rotation and produce a combined volume image from the first volume image and the second volume image.

7. A CT scanning apparatus according to claim 1 further comprising a support couch for a patient, to locate the patient substantially at the axis of rotation.

8. A CT scanning apparatus according to claim 6 in which the support couch further comprises a patient immobilisation system.

9. A CT scanning apparatus according to claim 7 in which the patient immobilisation system comprises an evacuatable bead bag.

10. A CT scanning apparatus according to claim 7 in which the patient immobilisation system comprises a bite post.

11. A CT scanning apparatus according to claim 7 in which the patient immobilisation system comprises a stereotactic frame.

12. A radiotherapeutic apparatus comprising;
a CT scanning apparatus according to claim 1,
a radiotherapeutic source mounted on the gantry at a location offset from the axis of rotation, and capable of emitting a beam of therapeutic x-radiation towards the axis of rotation.

13. A radiotherapeutic apparatus comprising an integrated CT scanning apparatus,
the CT scanning apparatus being according to claim 1, and
the x-ray source being capable of emitting x-radiation at a third x-ray energy being a therapeutic x-ray energy that is higher than both of the least two x-ray energies.

* * * * *